US011407978B2

(12) United States Patent
Shastri et al.

(10) Patent No.: US 11,407,978 B2
(45) Date of Patent: Aug. 9, 2022

(54) EXTRACELLULAR MATRICES WHICH CAN BE USED AS SCAFFOLD FOR LIVING CELLS

(75) Inventors: V. Prasad Shastri, Nashville, TN (US); Aurelien Forget, Freiburg (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 0 days.

(21) Appl. No.: 13/881,139

(22) PCT Filed: Aug. 18, 2011

(86) PCT No.: PCT/EP2011/064202
§ 371 (c)(1),
(2), (4) Date: Oct. 23, 2013

(87) PCT Pub. No.: WO2012/055596
PCT Pub. Date: May 3, 2012

(65) Prior Publication Data
US 2014/0038290 A1     Feb. 6, 2014

(30) Foreign Application Priority Data
Oct. 25, 2010   (EP) .................................... 10188774

(51) Int. Cl.
| | | |
|---|---|---|
| *C12N 5/077* | (2010.01) | |
| *C12N 5/0735* | (2010.01) | |
| *C12N 5/073* | (2010.01) | |
| *C12N 5/079* | (2010.01) | |
| *C12N 5/071* | (2010.01) | |
| *C12N 5/0775* | (2010.01) | |
| *C12N 5/074* | (2010.01) | |
| *C12N 5/00* | (2006.01) | |

(52) U.S. Cl.
CPC ......... *C12N 5/0655* (2013.01); *C12N 5/0068* (2013.01); *C12N 5/0605* (2013.01); *C12N 5/0606* (2013.01); *C12N 5/0618* (2013.01); *C12N 5/0621* (2013.01); *C12N 5/0625* (2013.01); *C12N 5/0653* (2013.01); *C12N 5/0654* (2013.01); *C12N 5/0657* (2013.01); *C12N 5/0661* (2013.01); *C12N 5/0662* (2013.01); *C12N 5/0676* (2013.01); *C12N 5/0679* (2013.01); *C12N 5/0684* (2013.01); *C12N 5/0696* (2013.01); *C12N 2533/50* (2013.01); *C12N 2533/70* (2013.01); *C12N 2533/72* (2013.01); *C12N 2533/74* (2013.01); *C12N 2533/76* (2013.01); *C12N 2533/80* (2013.01); *C12N 2537/00* (2013.01)

(58) Field of Classification Search
USPC ....................................................... 435/397
See application file for complete search history.

(56) References Cited

U.S. PATENT DOCUMENTS

| | | | |
|---|---|---|---|
| 10,968,285 B2 | 4/2021 | Shastri et al. | |
| 2004/0235027 A1* | 11/2004 | Lam ..................... | B01J 19/0046 435/6.16 |
| 2008/0286360 A1 | 11/2008 | Shoichet et al. | |
| 2009/0291912 A1* | 11/2009 | Tijsma ..................... | A61K 9/19 514/55 |
| 2014/0314722 A1 | 10/2014 | Shastri et al. | |
| 2021/0355247 A1 | 11/2021 | Shastri et al. | |

FOREIGN PATENT DOCUMENTS

| | | |
|---|---|---|
| WO | WO 02/18448 A2 | 3/2002 |
| WO | WO 03/74087 A1 | 9/2003 |
| WO | WO 2013/023793 A2 | 2/2013 |

OTHER PUBLICATIONS

Cao et al., Photomobilization of biomolecules within a 3-dimensional hydrogel matrix. Journal of Biomaterials Science, Polymer Edition, vol. 13, No. 6 (2002) pp. 623-636.*
Rowley et al., Alginate hydrogels as synthetic extracellular matrix materials. Biomaterials, vol. 20 (1999) pp. 45-53.*
Padmanabhan and Smith, A preliminary investigation of modified alginates as a matrix for gene transfection in a HeLa cell model. Pharmaceutical Development and Technology, vol. 7, No. 1 (2002) pp. 97-101.*
Markusen et al., Behavior of adult human mesenchymal stem cells entrapped in alginate-GRGDY beads. Tissue Engineering, vol. 12, No. 4 (2006) pp. 821-830.*
Bragd et al., TEMPO-mediated oxidation of polysaccharides: survey of methods and applications. Topics in Catalysis, vol. 27, Nos. 1-4 (Feb. 2004) pp. 49-66.*
Forget et al., Polysaccharide hydrogels with tunable stiffness and provasculogenic properties via α-helix to β-sheet switch in secondary structure. Proceedings of the National Academy of Sciences, vol. 110, No. 32 (Aug. 6, 2013) pp. 12887-12892.*
Ogawa et al., Three D structures of chitosan. International Journal of biological Macromolecules. Vol. 34, No. 1-2 (2004) pp. 1-8. (Year: 2004).*
Sterilization: Guideline for disinfection and sterilization in healthcare facilities [online]. Center for Disease Control and Prevention, 2008 [retrieved 2019-0719], Retrieved from the Internet:< URL: ttps://www.cdc.gov/infectioncontrol/guidelines/disinfection/sterilization/index.html>. (Year: 2008).*

(Continued)

*Primary Examiner* — Kara D Johnson
(74) *Attorney, Agent, or Firm* — Wolf, Greenfield & Sacks, P.C.

(57) ABSTRACT

The present invention discloses an extracellular matrix comprising a modified polysaccharide consisting of repeating disaccharide units whereby in at least 11% of the disaccharide units one primary alcohol group is oxidized into a carboxylic acid.

13 Claims, 8 Drawing Sheets
Specification includes a Sequence Listing.

(56) References Cited

OTHER PUBLICATIONS

Varoni et al., Agarose gel as biomaterial or scaffold for implantation surgery: Characterization, histological and histomorphometric study on soft tissue response. Connective Tissue Research, vol. 53, No. 6 (2012) pp. 548-554. (Year: 2012).*
*U.S. Appl. No. 17/198,081, filed Mar. 10, 2021, Shastri et al.
PCT/EP2011/064202, dated Feb. 29, 2012, International Search Report and Written Opinion.
PCT/EP2011/064202, dated May 10, 2013, International Preliminary Report on Patentability.
PCT/EP2011/064202, dated Mar. 22, 2013, International Search Report and Written Opinion.
PCT/EP2012/003504, dated Feb. 27, 2014, International Preliminary Report on Patentability.
International Search Report and Written Opinion dated Feb. 29, 2012 for Application No. PCT/EP2011/064202.
International Preliminary Report on Patentability dated May 10, 2013 for Application No. PCT/EP2011/064202.
International Search Report and Written Opinion dated Mar. 22, 2013 for Application No. PCT/EP2012/003504.
International Preliminary Report on Patentability dated Feb. 27, 2014 for Application No. PCT/EP2012/003504.
Afanassiev et al. Preparation of DNA and protein micro arrays on glass slides coated with an agarose film. Nucleic Acids Res. Jun. 1, 20005;28(12):E66.
Bragd et al. TEMPO-mediated oxidation of polysaccharides: survey of methods and applications, Topics in Catalysis, vol. 27, Nos. 1-4, Feb. 2004.
Bragd et al. Selective oxidation of carbohydrates by 4-AcNH-TEMPO/peracid systems. Carbohydrate Polymers. 2002. 49(4), 397-406.
Hassan et al. Acid-catalyzed oxidation of some sulfated polysaccharides: Kinetics and mechanism of oxidation of kappa-carrageenan by cerium(IV) in aqueous perchlorate solutions. J. Molecular Catalysis A: Chemical. Nov. 1, 2010. 332(1-2), 138-44.
Luo et al. A photolabile hydrogel for guided three-dimensional cell growth and migration. Nat Mater. Apr. 2004;3(4):249-53. doi: 10.1038/nmatl092. Epub Mar. 21, 2004.
Muzzarelli et al. 6-Oxychitins, novel hyaluronan-like regiospecifically carboxylated chitins. Carbohydrate Polymers, App Sci Publishers, Ltd. Aug. 1, 1999: 39(4), 361-7.
Rüther et al. Unravelling a Direct Role for Polysaccharide β-Strands in the Higher Order Structure of Physical Hydrogels. Angew Chem Int Ed Engl. Apr. 10, 2017;56(16):4603-4607. doi: 10.1002/anie. 201701019. Epub Mar. 23, 2017.
Tan et al. Injectable, Biodegradable Hydrogels for Tissue Engineering Applications. Materials (Basel). Mar. 10, 2010;3(3): 1746-67.
Bragd et al. Bromide-free TEMPO-mediated oxidation of primary alcohol groups in starch and methyl alpha-D-glucopyranoside. Carbohydr Res. Sep. 22, 2000;328(3):355-63.

* cited by examiner

Figure 1

| Name | Structure | Origin | Gelation mechanism |
|---|---|---|---|
| *Hyaluronic Acid* |  | Mammalian | use of crosslinker to form a 3D network |
| *Heparin sulfate* |  | Mammalian | |
| *Dermatan sulfate* |  | Mammalian | |
| *Chondroite sulfate* |  | Mammalian | |
| *Alginate* |  | Algae | $Ca^{2+}$ bridges |
| *Chitosan* |  | Marine shell | Repulsion of charges |
| *Pullulan* |  | Fungus | Like cellulose, sheet organization |
| *k-Carrageenan* |  | Algae | helices aggregation |
| *Agarose* |  | Algae | helices aggregation |

*Fig. 4*: A reaction mechanism of the D-Galactose primary alcohol oxidation into a carboxylic acid; B FTIR spectrum of the blue native Agarose and red modified Agarose; C MAS-NMR of the red modified Agarose and blue native Agarose; D percentage of modification determined by FTIR plot against the amount of base added to the reaction as a mean of 12 reactions, error bars represent the standard deviation.

Fig. 5: A temperature sweep of native Agarose, red and 60% modified Agarose, blue dotes represent G' and triangles G''; B frequency sweep of native Agarose, red and 60% modified Agarose, blue dotes represent G' and triangles G''; C temperature of gelation of Agarose of different percentage of modification; D shear modulus of Agarose of different percentage of modification. In all charts, the error bars represent the standard deviation, E: picture of 2% w/v gels respectively 1 native Agarose, 2 28% modified Agarose, 3 60% modified Agarose, 4 93% modified Agarose.

Fig. 6: A circular dichroism of red: native Agarose and blue :93% modified Agarose,;B circular dichroism of dashed: 93% Agarose at 5°C and plain 93% modified Agarose at 90°C; C circular dichroism of different modified gel of Agarose at 203 nm, D circular dichroism of dashed red : native Agarose, dashed blue - 93% modified Agarose, plain red native K-carrageenan, plain blue 93% modified k-carrageenan; E zeta potential of different modified Agarose; F blue: size and red: polydispersity measured by light scattering of diluted solution of different modified Agarose. In all charts, error bars represent the standard deviation.

Fig. 7: A RMSD from the first frame for red native Agarose and blue totally modified Agarose; B cumulated H bonds between the two strand of polysaccharide; C Ramachandran plot of native Agarose AG link in chain 1 and GA link in chain 2; D Ramachandran plot of totally modified Agarose AG link chain 1 and GA link in chain 2; E1 frame 1 of the MD simulation for native Agarose; E2 frame token from the middle of the simulation; F1 frame 1 of the MD simulation for totally modified Agarose; F2 frame token from the middle of the simulation.

*Fig. 8*: *Column A: native polysaccharide, B 28% of modification, C 60% of modification, D 93% of modification; Row 1 is the ESEM of 2% w/v freeze dried Agarose gel; Row 2 is the AFM picture of the height of Agarose gels, Row 3 is the 3D reconstruction of AFM pictures; Row 4 is the ESEM of 2% w/v freeze dried k-carrageenan gels at low magnification; Row 5 is the ESEM of 2% w/v freeze dried k-carrageenan at high magnification, E is the surface roughness of the AFM sample of Agarose gels against the percentage of modification.*

EXTRACELLULAR MATRICES WHICH CAN BE USED AS SCAFFOLD FOR LIVING CELLS

CROSS-REFERENCE TO RELATED APPLICATIONS

This application is a national stage filing under 35 U.S.C. 0 371 of International Patent Application Serial No. PCT/EP2011/064202, filed Aug. 18, 2011, which claims priority to European Patent Application No. 10188774.3, filed Oct. 25, 2010, each of which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION BY REFERENCE OF MATERIAL SUBMITTED ON A COMPACT DISC OR AS A TEXT FILE VIA THE OFFICE ELECTRONIC FILING SYSTEM (EFS-WEB)

The instant application contains a Sequence Listing which has been submitted electronically in ASCII format and is hereby incorporated by reference in its entirety. Said ASCII copy, created on Jul. 6, 2015, is named 4348-103US_SL.txt and is 989 bytes in size.

STATEMENT REGARDING PRIOR DISCLOSURES BY THE INVENTOR OR A JOINT INVENTOR

Not Applicable

BACKGROUND OF THE INVENTION

The present invention relates to extracellular matrices which can be used as scaffold for living cells.

Living cells of higher organisms reside in an environment that is mechanically and biologically well-defined by an extracellular matrix (in the following ECM). Structural and mechanical aspects of the matrix such as stiffness and topography can have a substantial influence on different cell functions like cell growth or differentiation of the cells. It is therefore desirable to provide extracellular matrices wherein important mechanical and chemical properties of the matrix can be influenced. It is for example interesting to lower the shear modulus or to improve the optical properties towards an increased transparency of the matrix.

The cell surrounding has been considered in the past decades as an important piece of the puzzle of organogenesis. It is known that each type of cell builds and evolves in a specific environment that provides the mechanical properties but also the nutritional needs of the cell. This environment is called extracellular matrix (ECM). Structural and functional molecules of the ECM can modulate cell behavior and function as well as which cell can interact with another in the human body. Nevertheless, most of these interactions are not fully understood. Therefore, a simpler model has to be developed in order to mimic human tissues in vitro. In a further aim this synthetic system has to be amenable to translation in vivo and should be capable of communicating with the body and aid in healing or regeneration of tissues.

The ECM (Extra Cellular Matrix) is defined as molecules composing the cell surrounding. In general ECM is made up of different components that can be classified as:
(1) the soluble molecules, e.g. growth factor and other signaling molecules and
(2) the structural polymers, composed of proteins and polysaccharides that gives the mechanical properties of the tissues.

It has been shown that the properties of this biopolymer matrix supporting the cell in the human body have many aspects (physical and chemical) that have been shown to impact the cell fate in vitro and in vivo. It has been found that in addition to cell adhesion moieties and growth factors, the physical attributes of a cellular microenvironment namely, stiffness and topography are another important element in dictating and controlling cell fate and function. Therefore, injectable, biologically well-defined systems with tailor-made and tunable physical properties are the evolutionary next-step in synthetic niches for cells.

Some synthetic ECM have already been commercialized. So far three different strategies have been explored to produce synthetic ECMs:
(1) Animal protein extracts; such as Matrigel which suffer from a lack of batch to batch reproducibility and a poor definition of the components which render difficulties in the interpretation of results.
(2) Synthetic polymers; such as degradable polyester that although biocompatible are not easy to synthesize and manufacture and additionally, require knowledge in synthetic chemistry to set it up and are also difficult to translate into in vivo clinical settings and
(3) Natural components of the ECM such as collagen or hyaluronic acid, which reproduce only one aspect of the natural ECM environment.

Various polysaccharides have been explored as ECMs for several decades. Prominent among them are hyaluronic acid, alginate acid and chitosan. Hyaluronic acid when modified by etherification using long chain alcohols can yield gels that are formed due to physical cross-links established by the aggregations of the hydrophobic alkyl chains in water. Hyaluronic acid can also be gelled using covalent crosslinking. In this case, the hyaluronic acid is oxidized to bear aldehyde groups which are then reacted with N-succiyl modified Chitosan or other biopolymers. Also, this cross-linking can be induced by diamine through Schiff base formation. Alginic acid can be processed into gels that can serve as cell supports by ionic crosslinking divalent cations.

BRIEF SUMMARY OF THE INVENTION

The present invention relates to extracellular matrix comprising a modified polysaccharide consisting of repeating disaccharide units whereby in at least 11% of the disaccharide units one primary alcohol group is oxidized into a carboxylic acid.

BRIEF DESCRIPTION OF THE SEVERAL VIEWS OF THE DRAWINGS

FIG. 4A shows a reaction mechanism of the D-Galactose primary alcohol oxidation into a carboxylic acid;

FIG. 4 B shows an FTIR spectrum of the native Agarose (blue) and modified Agarose (red);

FIG. 4C shows MAS-NMR of modified Agarose (red) and native Agarose (blue);

FIG. 4 D shows the percentage of modification determined by FTIR plot against the amount of base added to the reaction;

FIG. 5 A shows a temperature sweep of native Agarose (red) and 60% modified Agarose (blue); dots represent G' and triangles represent G";

FIG. 5B shows a frequency sweep of native Agarose (red) and 60% modified Agarose (blue), dots represent G' and triangles G";

FIG. 5 C shows the temperature of gelation of Agarose of different percentage of modification;

FIG. 5 D shows the shear modulus of Agarose of different percentages of modification.

FIG. 5 E: shows pictures of 2% w/v gels respectively: 1 native Agarose, 2 28% modified Agarose, 3 60% modified Agarose, 4 93% modified Agarose;

FIG. 6 A shows the circular dichroism of native agarose (red) and 93% modified agarose (blue);

FIG. 6 B shows the circular dichroism of 93% modified agarose at 5° C. (dashed line) and 90° C. (plain line)

FIG. 6 C shows the circular dichroism of different modified agarose gels at 203 nm;

FIG. 6 D shows the circular dichroism of native agarose (dashed red line) and 93% modified agarose (dashed blue line) and native k-carrageenan (plain red line) and 93% modified carrageenan (plain blue line);

FIG. 6 E shows the zeta potential of different modified agarose;

FIG. 6 F shows the polydispersity of different modified agarose measured by light scattering;

FIG. 7 A shows a RMSD form native agarose (red) and totally modified agarose (blue)

FIG. 7 B shows the cumulated H bonds between the two strands of polysaccharide;

FIG. 7 C shows a Ramachandran plot of native Agarose AG link in chain 1 and GA link in chain 2;

FIG. 7 D shows a Ramachandran plot of totally modified Agarose AG link in chain 1 and GA link in chain 2:

FIG. 7 E1 shows frame 1 of the MD simulation for native Agarose;

FIG. 7 E2 shows a frame taken from the middle of the simulation;

FIG. 7 F1 shows frame 1 of the MD simulation for totally modified Agarose, and

FIG. 7 F2 shows a frame taken from the middle of the simulation.

DETAILED DESCRIPTION OF THE INVENTION

It is an essential component of the extracellular matrix of the present invention to contain at least one modified polysaccharide whereby the polysaccharide consists of repeating disaccharide units. In a preferred embodiment the modified polysaccharide is derived from agarose. Agar is a structural polysaccharide of the cell walls of a variety of red seaweed. It consists of two groups of polysaccharides, namely agarose and agaropectin. Agarose is a neutral, linear polysaccharide with no branching and has a backbone consisting of 1,3-linked β-D-galactose-(1-4)-α-L-3,6anhydrogalactose repeating units. This dimeric repeating unit, called agarobiose differs from a similar dimeric repeating unit called carrabiose which is derived from carrageenan in that it contains 3,6-anhydrogalactose in the L-form and does not contain sulfate groups.

Figure 1:
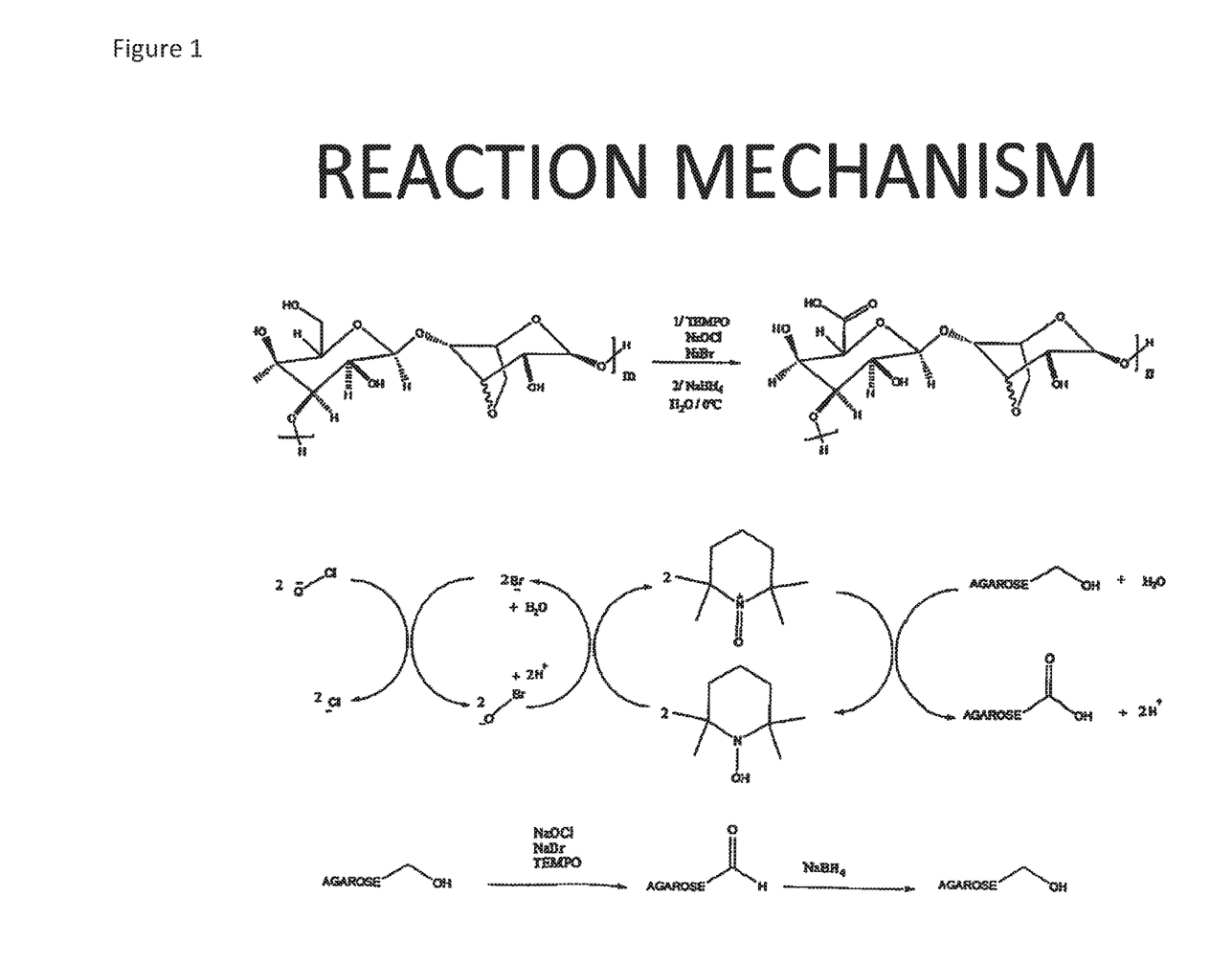
FIG. 1 shows a schematic reaction mechanism for the oxidation of the primary hydroxyl groups in disaccharides into carboxylic acid groups.

Such dimeric repeating units derived from naturally occurring polysaccharides are chemically modified by the specific oxidation of the primary hydroxyl group into a carboxylic acid. One reaction mechanism is schematically shown in FIG. 1. It goes without saying that the specific oxidation can be also performed by other reactions which are well-known to the chemist.

Depending on the reaction conditions it is possible to oxidize a certain percentage of the primary hydroxyl groups. According to the invention at least 11% of the disaccharide units are oxidized. In a preferred embodiment at least 20 up to 99% of the disaccharide repeat units of the primary alcohol groups are oxidized into a carboxylic acid. In a particularly preferred embodiment in 50-95% of the repeat disaccharide units the primary alcohol group is oxidized into a carboxylic acid group.

In order to determine as precisely as possible the percentage of the oxidized primary alcohol groups it is possible either to perform the oxidation reaction in a controlled manner or alternatively the polysaccharide is oxidized completely so that about 100% of the primary alcohol groups are oxidized. Such completely oxidized polysaccharide can be blended with unmodified polysaccharide which may either be the same polysaccharide or another polysaccharide. Since the chemical modification can be precisely controlled and by controlling the blending with another polysaccharide or the same unmodified polysaccharide it is possible to control the chemical properties of the extracellular matrix.

One important aspect is the shear modulus which can range according to the present invention from about 10 Pa which reflects the structure of a nerve tissue to about $10^7$ Pa which corresponds with the shear modulus of cartilage tissues. By blending gels of different extent of chemical modification the nanoscale structure of the gel can be impacted. It has been shown that nanoscale topography influences cell shape, cytoskeletal assembly and function. The shear modulus of the extracellular matrix ranges preferably from 1 Pa to 100 kPa and more preferred from 1 Pa to 50 kPa and in a most preferred embodiment in a range from 10 Pa to 10 kPa.

In an especially preferred embodiment agarose wherein the primary alcohol group has been oxidized in a carboxylic acid group is blended with non-modified agarose.

Agarose has been mainly used for separation techniques such as electrophoresis, Gel Permeation Chromatography, High Performance Liquid chromatography but also as additive in food. Recently the use of this hydrogel for engineered ECM has shown interesting behavior. Agarose has been successfully used to engineer cartilage de novo which suggest that further development will offer the possibility to regenerate other tissues. It has been shown that agarose gels induce bone reconstruction in vivo. It has also been shown that it is possible to modify the agarose backbone by oxidizing the C6 position of the D-galactose residue in a specific way. This modification enables grafting of molecules on the agarose gel through a carboxylic acid which is highly valuable for biochemistry. It has been observed that the oxidation of the C6 primary alcohol of the D-galactose residue induces a loss of shear modulus but also a weaker gel. The design of new material using Agarose has been investigated by creating copolymer of Agarose-Collagen, or Agarose-Cellulose, but also by blending Agarose with natural polymer of the ECM.

Figure 2:
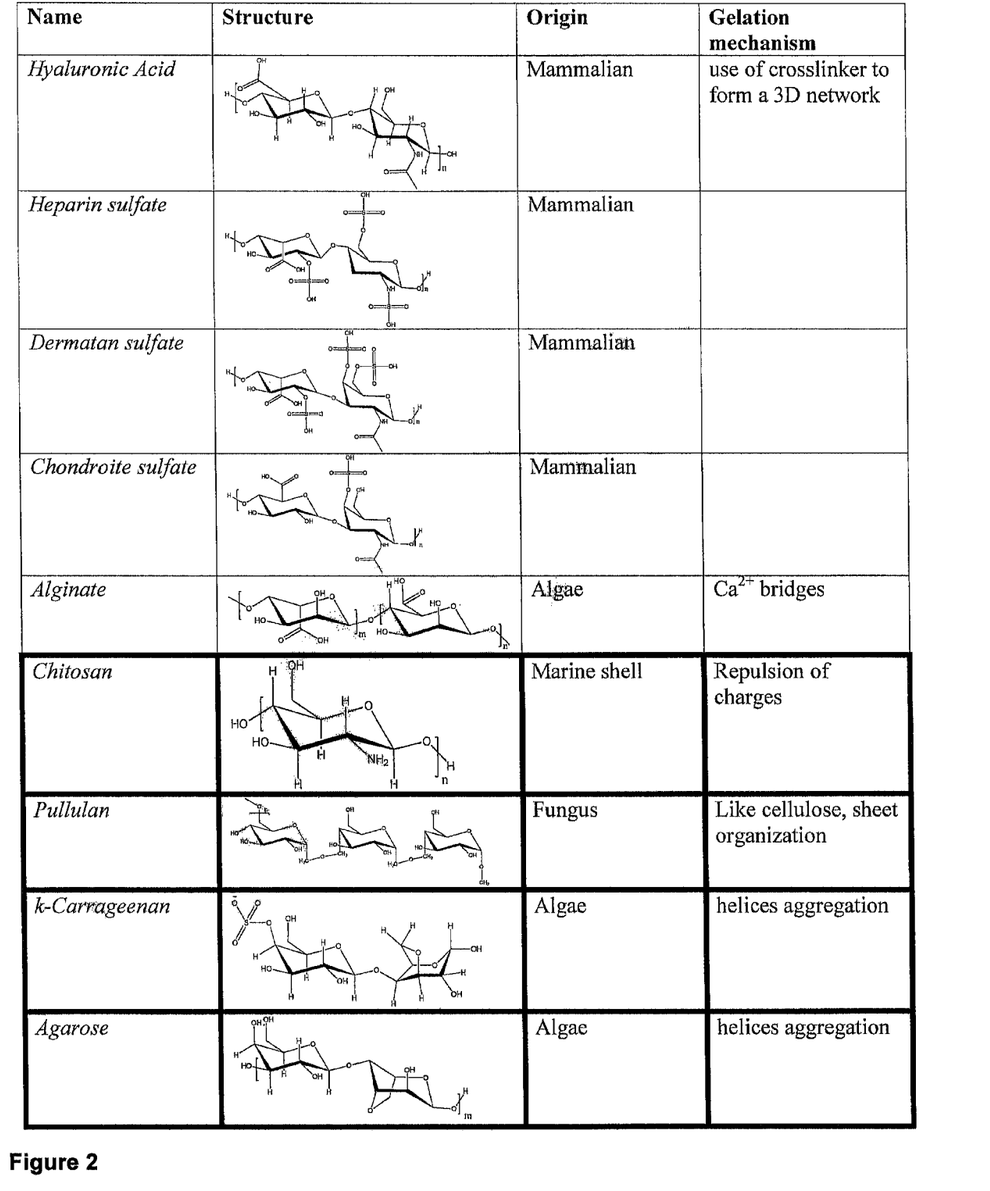
FIG. 2 shows a table with poylsaccharides suitable for use in the present invention.

Also agarose is the preferred component of the extracellular matrix of the present invention. It is also possible to use other polysaccharides of natural origin as component which can be blended with modified agarose if such component cannot be oxidized as described above. If the structure contains a primary hydroxyl group which can be oxidized into a carboxylic acid group the repeating disaccharide units can be modified as described above in more detail for agarose. Other polysaccharides which can be used in the present invention are shown in FIG. 2. In particular the polysaccharides are hyaluronic acid, heparin sulfate, dermatan sulfate, chondroite sulfate, alginate, chitosan, pullulan, k-carrageenan. In the most preferred embodiment agarose is used.

In a preferred embodiment the extracellular matrix can be used in order to grow cells in a three-dimensional structure which resembles the natural situation. Cells, preferably human cells, which are preferably selected from the group consisting of chondrocytes, osteoblasts, osteoclast, skin epithelial cells, intestinal epithelial cells, corneal epithelial cells, astrocytes, neurons, oligodendrocytes, smooth muscle cells, endothelial cells, cardiomyocytes, pancreatic islet cells, kidney epithelial cells, embryonic stem cells, pluripotent stem cells; or naïve cells obtained from umbilical cord.

In a particularly preferred embodiment the extracellular matrix can be used whereby the cells, preferably human cells, are stem cells which have the ability to differentiate into the desired cells. This can be achieved by adding such cytokines which lead to the development of the desired tissue. The stem cells may be embryonic stem cells whereby such stem cells are excluded which can be prepared exclusively by a method which necessarily involves the destruction of the human embryos from which said products are derived. Consequently only such embryonic stem cells are encompassed by the present invention which comply with the requirements of the decision of the Enlarged Board of Appeal G 2/06. In particularly preferred embodiments the stem cells are somatic stem cells which may for example be adipose-derived. In another embodiment reprogrammed pluripotent somatic cells are used. In another embodiment amniotic stem cells are used in the extracellular matrix.

By using the extracellular matrix of the present invention and using the desired cells it is possible to build well-defined three-dimensional tissues which are influenced by the physicochemical properties of the matrix.

The extracellular matrix of the present invention can be used either for experimental purposes since the interaction of cells and its understanding gains more and more importance in many fields of biological research. Alternatively, the extracellular matrix can be used in order to produce artificial tissues. It is for example possible to grow the cells as described above in order to produce artificial three-dimensionally linked tissues which can be used as implant for the curing of various defects. It is for example possible to produce homologous bone structures by cultivating osteoblasts and/or osteoclasts in the extracellular matrix as described herein. Alternatively, artificial skin or cartilage can be produced. Since the material is well compatible with the immune system, no unexpected allergic reactions can be expected. This is especially true when homologous cells are used for the preparation of artificial tissues.

In a particularly preferred embodiment the extracellular matrix of the present invention is used as a regenerative implant. Such a regenerative implant is produced in vitro by using the matrix as a scaffold for the tissues which grow three-dimensionally in vitro. After the implant has reached the desired structure it can be implanted into a patient. Since the form of such an implant can be precisely designed by using the appropriate stiffness and viscosity or the required modulus usually in the first step the matrix is formed as a scaffold having the desired form. This extracellular matrix may be present in various forms. Sheets with a defined thickness are incubated with dermal cells and artificial skin can be produced thereby. Tubes having a well-defined diameter are incubated with suitable cells which form blood vessels like endothelial cells in order to produce artificial arteries or veins.

It is possible to form tubular structures which are brought into contact with such type of cells which form blood vessels. Alternatively, the extracellular matrix may have the form of a disc and the matrix will be brought into contact with cells which form cartilage tissues. Since the mechanical properties like stiffness, rigidity and viscosity of the extracellular matrix can be controlled by selecting the appropriate ratio of modified polysaccharide:unmodified polysaccharide, in particular modified agarose:unmodified agarose, the properties can be regulated very precisely. It is a further advantage of the present invention that the three-dimensional structure of the tissue is given by the extracellular matrix. Therefore, thickness, length or any other desired form of the matrix can be prepared by using a suitable form or mold. For medical purposes it is preferred to sterilize the agarose. This can be done either by appropriate chemicals or more preferred by heat treatment or by radiation.

After the extracellular matrix has been brought into the desired form and the form has been sterilized it is brought into contact with the desired cells, preferably in the appropriate medium which contains the desired growth factors. Depending on the type of cell which grows on the extracellular matrix, appropriate cytokines are added. It is also possible to add sequentially two different types of cells in order to form an extracellular matrix wherein tissues have been grown which resemble the part of the body which should be replaced or supported as far as possible. Such extracellular matrices wherein tissue cells have been grown to form tissues can be used as regenerative implants in the treatment of humans. It is possible to produce by using the extracellular matrix of the present invention regenerative implants which can be used as artificial skin, as artificial blood vessels or for the replacement of nerve tissues. It is also possible to produce mucosal tissues or parts of the eye, in particular artificial lenses. A particular advantage of the present invention is that the extracellular matrix has superior optical quality which means that the extracellular matrix can be completely clear. This is extremely important for forming artificial cornea and/or lenses.

In another embodiment of the present invention the extracellular matrix can be used for producing delayed release formulations of pharmaceutically active components. By varying the mechanical properties of the extracellular matrix the product can be tailored to the desired purpose. If for example the extracellular matrix is very stiff, pharmaceutical agents which are included within the matrix will be delivered after implantation into the body very slowly.

On the other hand, if the viscosity and the stiffness of the extracellular matrix is rather low, a pharmaceutical agent which is entrapped in the extracellular matrix will be released rather quickly.

In a further embodiment the extracellular matrix of the present invention can be used with pharmaceutically active agents like growth factors, insulin, biologically active peptides, chemokines, cytokines, steroids, antibiotics, analgesics and anti-inflammatory agents or anti-cancer drugs.

In a further embodiment the extracellular matrix can also be used for diagnostic purposes by including imaging agents as e.g. MRE contrast agents, CT contrast agents, fluorescent imaging probes or radio nuclei. By including those agents into the extracellular matrix and applying thereafter the matrix to the human body the agents are trapped into the extracellular matrix and can be released in a controlled manner by adjusting the properties of the matrix like viscosity, stiffness and form which depends on the intended use.

It is also possible to include into the matrix cells which form a tissue and pharmaceutically active agents.

In further preferred embodiments the carboxylic group which is derived from the oxidation of the primary hydroxyl group is covalently coupled with a peptide sequence. In preferred embodiments the peptide sequence is selected from the group consisting of the cell adhesion sequence arginine-glycine-aspartic acid, the peptide sequences IKVAV (SEQ ID NO: 1) and YIGSR (SEQ ID NO: 2) or a protein which is preferably selected from collagen, collagen fragments, fibronectin and mixtures thereof.

In another preferred embodiment the extracellular matrix may contain a modification of the carboxylic acid group derived from the oxidation of the primary hydroxyl group insofar that this carboxylic acid group is covalently linked to a nucleic acid sequence. The nucleic acid sequence may be single-stranded DNA, double-stranded DNA, single-stranded RNA and siRNA. The nucleic acid may serve as click chemistry. In case single-stranded nucleic acids are linked to the extracellular matrix, such single-stranded molecules may hybridize to complementary single-stranded molecules which are linked to other components. This offers the opportunity to easily attach molecules or even whole cells to the extracellular matrix. Depending on the purpose of the use of the extracellular matrix it may be very helpful to include specific points of fixation into the extracellular matrix which can be designed according to the intended use of the extracellular matrix.

The present invention describes the ability to change the tertiary structure of polysaccharides in a manner that the roughness, stiffness, thermal gelation behavior and optical feature of the material can be finely tuned to target a specific material. The modification made on the backbone consists of an oxidation of the primary alcohol of agarose backbone into a carboxylic acid. It was demonstrated that this modification induces a change of organization of the polymer backbone and has been replicated in k-carrageenan as another polysaccharide. The gel of interest can be obtained by controlling the amount of chemical modification of the backbone but also by blending the native polysaccharide with a fully modified form. This results in a uniform material with feature such as stiffness, thermal gelation and roughness that can be adjusted by incorporating different amounts of each polysaccharide.

Figure 3:
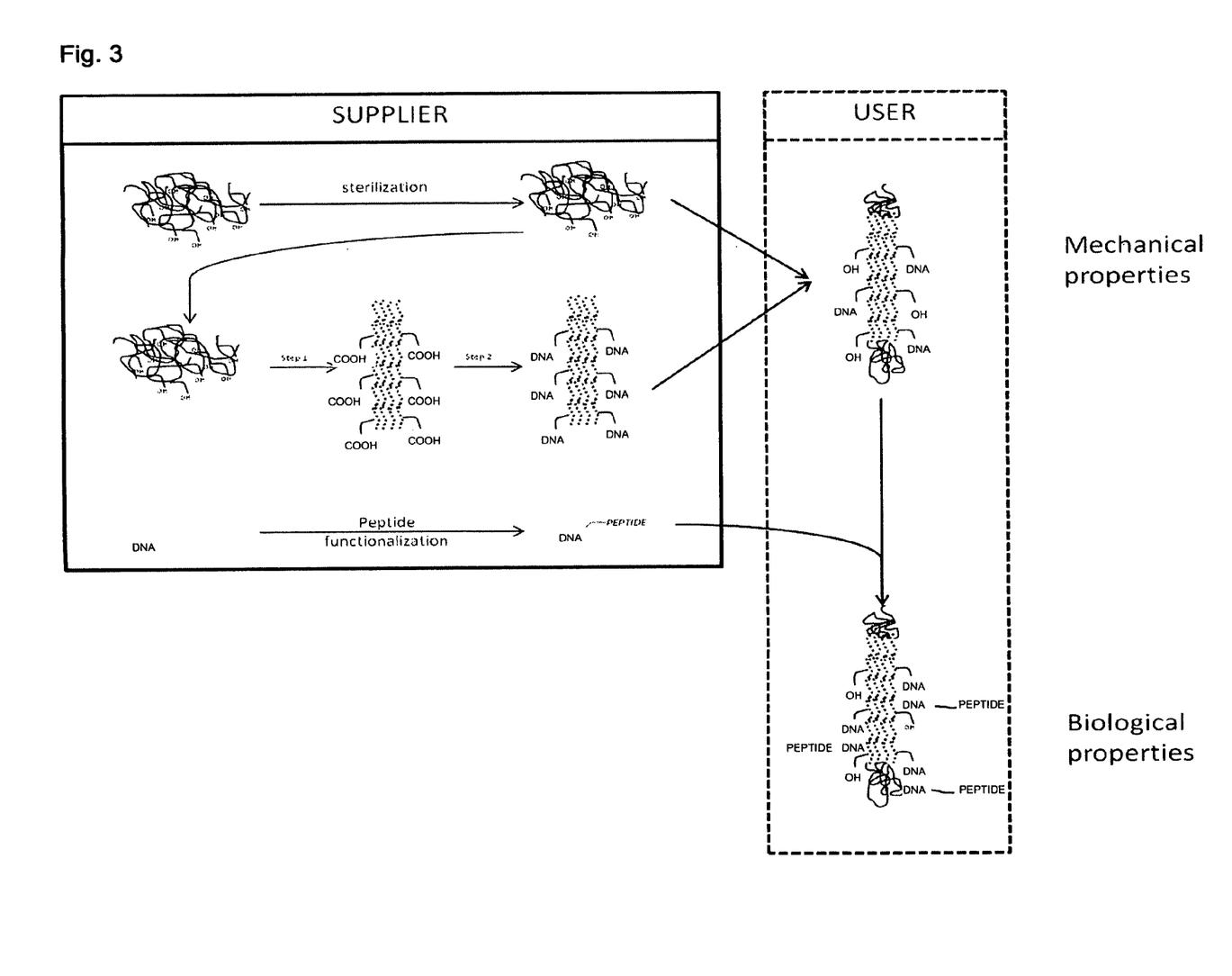
FIG. 3 shows how an oligo-DNA strand can be coupled to the polymer backbone with the complementary oligo-DNA strand that has been previously chemically bound to the peptide of interest.

The ease of control of the physical properties enables the design of an environment which is mechanically similar to natural human tissue but also biologically neutral since the agarose does not interact with cells. In case it is desired that cells interact with the material, biological ligands that are recognized by cells have to be grafted on the polymer backbone. Therefore two strategies have been followed, first the chemical way by using EDC coupling that allows direct chemical binding between the carboxylic acid moieties to the terminated amine of a peptide. The second approach has been made with DNA coupling that enables an easier manipulation for the final user. An oligo-DNA strand can be coupled to the polymer backbone with the complementary oligo-DNA strand that has been previously chemically bound to the peptide of interest. This way of binding is for the final user a step forward to a fully tunable system, where the mechanical properties can be adjusted by mixing two components (native with modified polysaccharide) and the biological signal incorporated to the backbone polymer by adding a component to the system (the complementary oligo-DNA strand bounded to the peptide of interest). This principle is shown in FIG. 3.

Preferred Embodiments of the Invention

Figure 4:
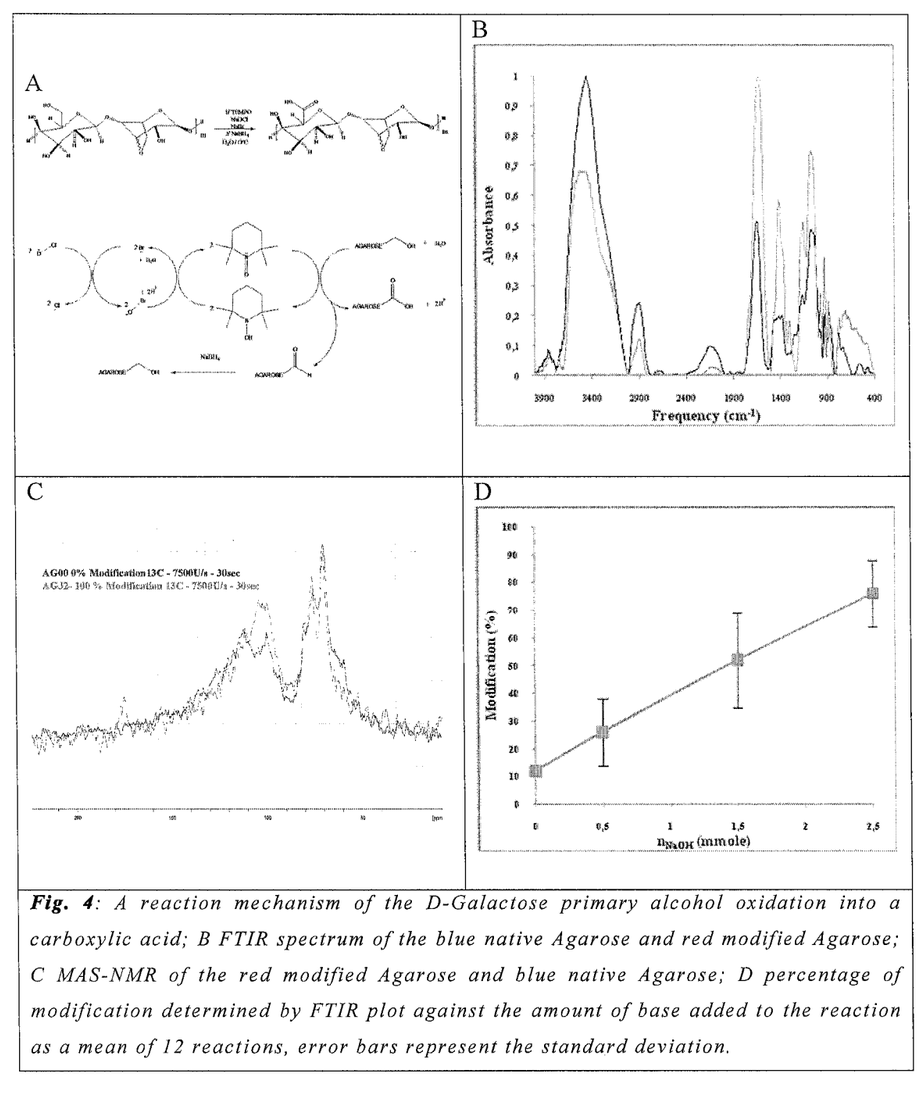

First the Agarose has been prepared by following protocols already published. The addition of NaOH during the reaction maintain the optimal pH of the reaction and compensate the acidification of the solution by the creation of carboxylic acids with the oxidizer TEMPO ((2,2,6,6-Tetramethyl-piperidin-1-yl)oxyl) reactivated with NaOCl and catalyst by the KBr, FIG. 4 A. The NaOH is used to maintain the optimal pH of 10.8 for the reaction, but also gives a quantitative characterization of the amount of carboxylic acid formed as it compensates the formation of the acidic moiety. Therefore a relation between the volume of base added and the quantity of carboxylic acid formed can be considered, equation 1. The probable side reaction that consist of the oxidation of the carboxylic acid down to the aldehyde is neutralized at the end of the oxidation by adding $NaBH_4$ which reduce the freshly reacted aldehyde back into a primary alcohol.

$$\frac{m_{Agarose}}{M_{n_{Agarose}}} \times DPI_{Agarose} = n_{NaOH} \qquad (1)$$

In order to have precise and reliable result, the characterization of the synthesis has been conducted by using different techniques. As a first qualitative analysis the $^{13}C$ MAS-NMR shows the appearance of a peak at 180 ppm, characteristic of the carboxylic acid, and the vanishing of the peak at 55 ppm characteristic of the primary alcohol. The quantitative method, FTIR, shows the increase of the ratio between the peaks at 1650 $cm^{-1}$: vibration band of the double bond carbon oxygen and 1360 $cm^{-1}$: the vibration band of the carbon oxygen from the primary alcohol, FIG. 4 B. The relative amount of carboxylic acid and primary alcohol can be calculated by integrating the peak of interest and using the equation (2).

$$\% \text{ Oxidation} = \frac{\int V_{C=O}}{\int V_{C=O} + \int V_{C-OH}} \quad (2)$$

The formation of carboxylic acid along the polysaccharide backbone is monitored by the amount of NaOH during the reaction and afterwards by the quantitative analysis using FTIR spectrometry. In order to compare both of the technique, the amount of NaOH added to the reaction against the calculated modification using FTIR has been plotted given a linear relation that show the accuracy of the both methods but also the reproducibility of this synthesis, FIG. 4 D.

It is assumed that the incorporation of ligands at the primary alcohol of the C6 position on the D-galactose of the Agarose repetition unit leads to a lower shear modulus and a lower temperature of gelation. In order to characterize in which manner the introduction of carboxylic groups on the polysaccharide backbone induces the change of mechanical and gelation properties a systematic rheological study of the gels has been conducted.

Figure 5:
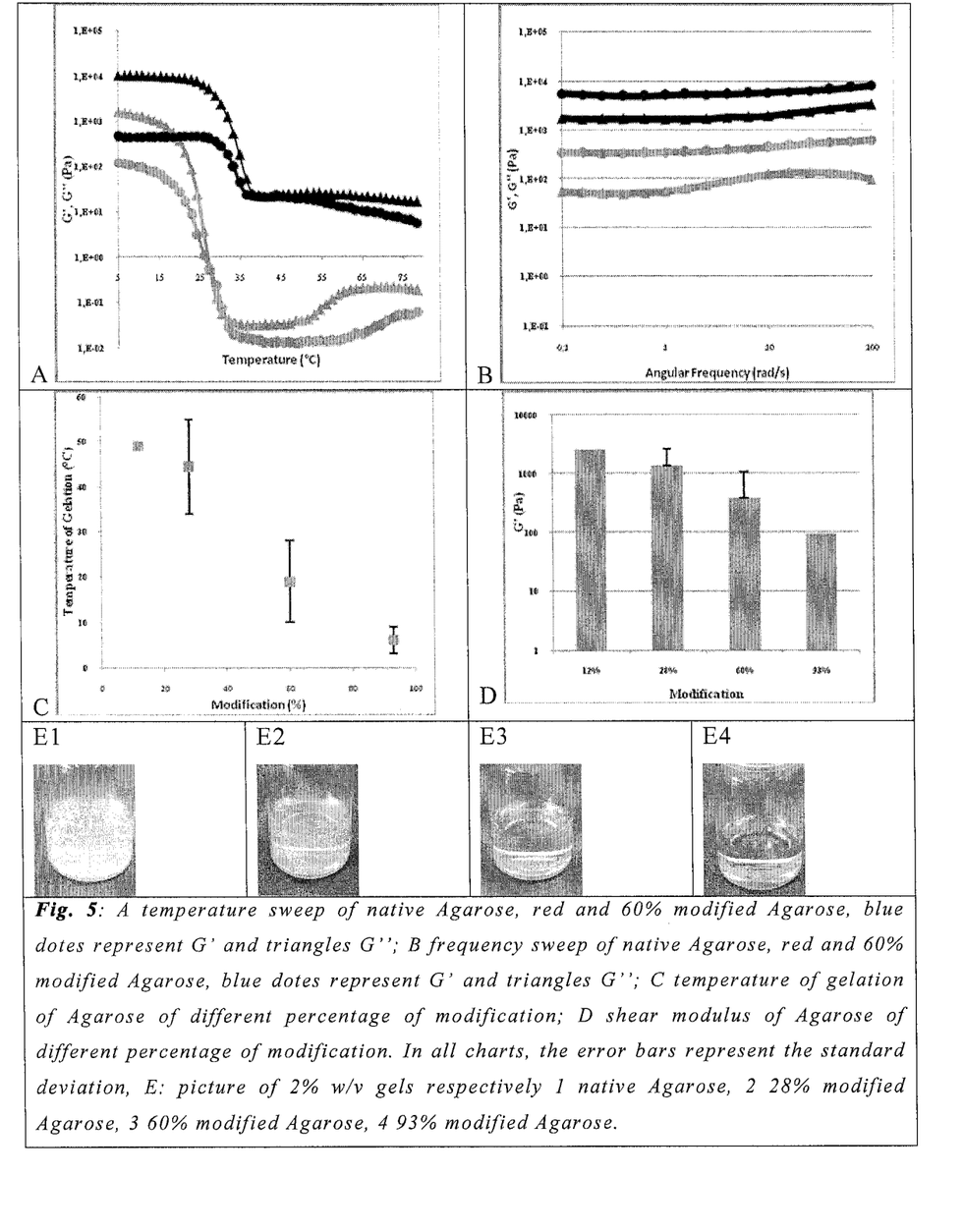

The gelation point, also named temperature of gelation, is determined by the equality of the shear storages to the loss moduli at a constant shear frequency and deformation with decreasing the temperature as shown in FIG. 5 A. Compared to the technique of the inverted bottle the temperature sweep is an objective measure that gives a more precise value. The increase of modification lowered the gelation temperature in a linear way. The difference of gelation temperature from native agarose of 40° C. to 93% modified down to 5° C. gives interesting features that can be used to tune the gelation temperature of the gel, see FIG. 5 C. Moreover the agarose forms a hydrogel that has a hysteretic behavior, i.e. the formation of physical crosslinked points happened at a lower temperature as the breakdown of the gel, which gives a particular thermal stability that makes it an interesting material for biological application.

The gel stiffness can be characterized by doing a frequency sweep, shear of the gel at a constant deformation and temperature with a frequency increase. In rheology a gel state can be defined as state where the shear and loss moduli are both independent of the shear frequency, FIG. 5 C. The modification of the polysaccharide backbone induces a lower shear and loss moduli which result of a weaker gel. This weakening of the polymer network seems to be related to the incorporation of carboxylic group, as the loss of primary alcohol provokes a linear loss of stiffness (FIG. 5 D).

The versatile stiffness of the gel can be compared to the human tissue stiffness. The different mechanical properties of the cell surrounding have been reporting to vary from $10^5$ Pa for bones down to $10^1$ Pa for nerves. The magnitude order of the gel stiffness covered by the different proportion of modification goes from $10^4$ Pa for a 2% w/v gel of native agarose down to $10^2$ Pa for a 93% modified gel of the same concentration.

It is known that the agarose backbone folds in an alpha-helix and that the gel is formed by the aggregation of these helices. The loss of rigidity of the different gels for a given concentration could be attributed to a loss of aggregation of the alpha helix. Moreover, the loss of the gel turbidity attributed to the amorphous structures formed by the aggregates reinforce the hypothesis of a loss of crosslinked point (see FIG. 5 E 1 to E 4).

Figure 6:
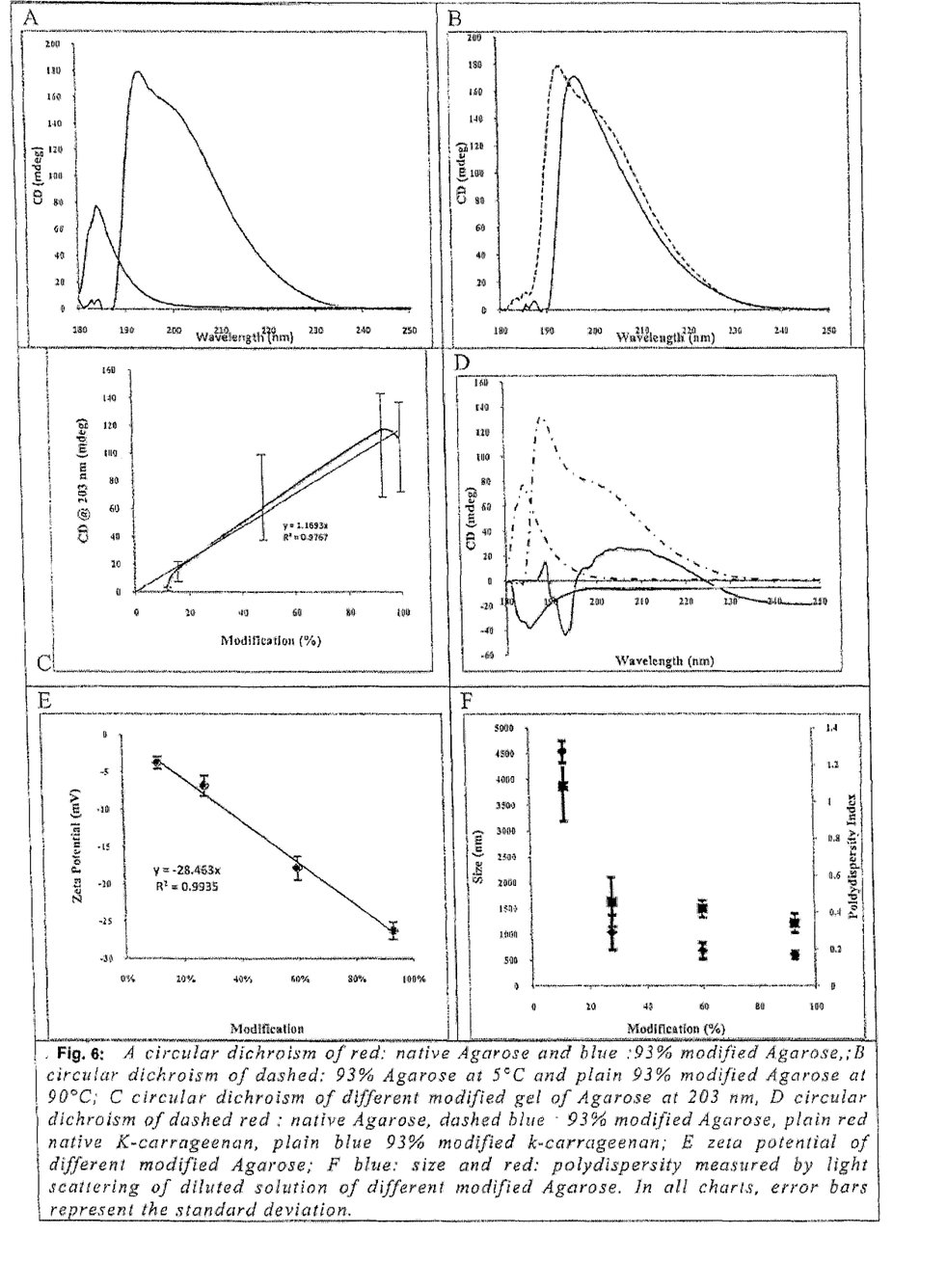

It has been suggested in the literature that the physical crosslinked point formed in the agarose hydrogel can be assimilated as spherical nanoparticles and then be characterized with SLS (static light scattering). It appears that the increase of the modification along the polymer backbone dramatically decreases the size of this crosslinked point but also their polydispersity resulting in smaller aggregates of a smaller size distribution, see FIG. 6 F. These results support the hypothesis of less aggregation of alpha-helix, but the loss of polydispersity is also a quantification of the organization of the aggregate. The decrease of the polydispersity reveals that the aggregates are organized in a more regular shape.

On the other hand, the measurement of the zeta-potential gives information of the mobile charges present on the polymer surface. It appears that the increase of the modification is linearly proportional to the increase of the zeta potential, see FIG. 6 E. The increase of the zeta potential transcript the incorporation of repulsion charges between the polymer chains that might disrupt the aggregation of the alpha-helix domains.

In the past, the alpha helix of the agarose has been characterized by using circular dichroism (CD). The native agarose CD is composed of a single peak at 185 nm that is characteristic of an alpha-helix conformation of the secondary structure. In order to understand the gelation mechanism of the modified Agarose, CD has been measured for different modified agarose preparations. It appears that the peak characteristic of an alpha-helix is shifted to higher wavelength and a new peak appears at 203 nm, see FIG. 6 A. The hypothesis of a lower number of alpha-helix aggregate will have lead to a reduced ellipticity in the alpha-helix area of the spectrum, but the shift of the spectrum to another area suggest a change of the folding of the modified agarose. The analogy of the conformation of polysaccharides with the folding of protein gives an indication of the new secondary structure of the modified agarose. Indeed the area of 203 nm correspond to the organization of proteins in beta-sheet. The consistent study of different modified gel highlight that the appearance of the new peak is linearly proportional to the amount of carboxylic acid along the polysaccharide backbone, see FIG. 6 C. The modification of the primary alcohol into a carboxylic acid clearly induces a change of the secondary structure into the agarose that is still able to form a gel at low temperature. The CD spectrum of the modified agarose has been done at two different temperatures, at 5° C. where the modified agarose is below its sol-gel transition temperature and at 90° C. above its gel-sol transition temperature. It appears that at high temperature the new peak at 203 nm vanished. The agarose made a gel that is temperature dependent, the temperature dependency of the new peak suggest that the gel dependency is now driven by this new organization and not anymore by the aggregation of the alpha-helix.

Agarose is not the only polysaccharide which exhibits an alpha-helix structure. Indeed the family of the carrageenan is also known to organize in alpha-helices and form also physical gels that are temperature dependent. The same spectroscopy study has been followed to characterize the k-Carrageenan that has been oxidized at the same position, according the same protocol than the agarose. The peak of the unmodified k-carrageenan and unmodified agarose are of opposite sign due to the different helix rotation, but both of them are in the same wavelength. The CD curves obtained for the modified k-carrageenan exhibit the same new peak at the same wavelength of 203 nm, see FIG. 6 D. The possibility to obtain the same CD behavior for two polysaccharides of the same family implies that the modification of this primary alcohol in theses polymers can be a general method to induce a beta-sheet like structure in polysaccharides.

Figure 7:
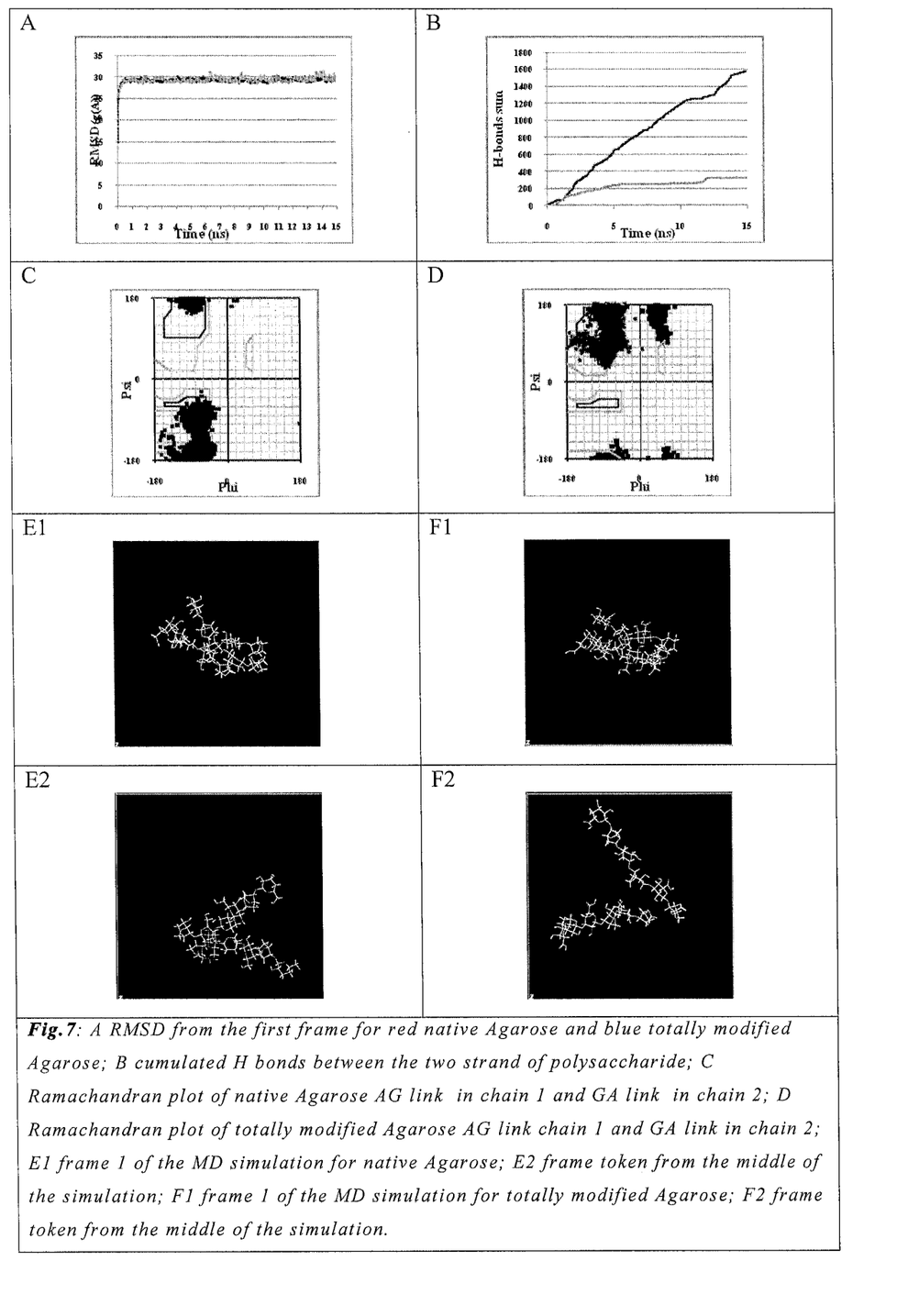

In order to validate these hypotheses a molecular dynamic simulation of two polysaccharides backbones over 15 ns has been ran. Past studies on polysaccharide have demonstrated the relevance of the molecular dynamic simulation. It is of high importance to validate the model of the new organization of the modified agarose. The root mean square deviation of the geometry from its initial position show that after 2 ns a stable conformation is obtained and will remain stable until the end of the simulation, see FIG. 7 A. In order to characterize the distance between the two polysaccharides strands the formation of h-bond between these two strands has been calculated. The formation of an h-bond is driven by the distance of an electronegative atom to a hydrogen atom. Each h-bond on each frame has been summed and this sum has been plotted against the time. Therefore a stable h-bond sum transcript the non presence of any h-bond, see FIG. 4 B. This calculation shows that the native agarose is able to form h-bond all along the simulation, but the totally modified agarose strands do not form any h-bonds after 5 ns, highlighting that the two polymer chains are too far from each other in order to interact together in this manner. The non interaction of the two polymer strands confirms the data obtained from the zeta potential that show repulsion forces between the two strands.

The main question that has to be answered by the simulation is the physical and geometrical possibility to form a beta-sheet structure. In past studies the conformation of the sugar cycles of the polymer chain has been analyzed using a Ramachandran plot. The dihedral angle of the glycosylic linkage can be plotted and compared with the cartography obtained for protein folding. The native agarose has its dihedral angle formed by the anhydrogalactopyranose/galactose bound of the chain 1 and galactose/anhydrogalactopyranose bound of the chain 2 in the alpha helix domain, see FIG. 7 C. The same bounds on the modified agarose have their dihedral angles in the beta sheet area of the plot, see FIG. 7 D. The change of area of the dihedral angles that switch from the alpha-helix position, to the beta-sheet location show that this suggested organization from the other analysis is possible. The animations created by the software give an idea about the polymers chains position along the time of the simulation. The conformation of the polymer of the first frame has been obtained from the x-ray data of the agarose. The two polymers have been modeled with the same initial conformation, see FIG. 7 E1 and F1. It appears that the chains of the native agarose are staying together along the simulation time, see FIG. 7 E2, but the chains of the modified agarose are repulsed from each other and position their carboxylic acid opposite from each other, see FIG. 7 F2.

The molecular dynamic simulation attests the possibility of this beta sheet conformation. As for the CD data, the plot of the dihedral angles is based on the theory developed for protein. The use of the specific area of the Ramachadran plot in order to describe the folding of protein has only by used so far, for protein. As the organization of the chains of polymer changes from an aggregation of alpha-helix to a beta-sheet, the impact on the macrostructure of the material should be non negligible.

The investigation of the macrostructure of the gel has been done by using an ESEM, see FIG. 7 A1 to D1. The highest difficulty in the study of gels is the difficulty to reveal the hydrated structure of the polymer network. Therefore freeze dried sample have been used for the electron microscope. The change of structure between the native and the modified agarose shows a radical change of their structure. The unorganized fibers of the native agarose leave the place to a highly ordered fibril structure as the percentage of modification of the polymer backbone is increased. The unorganized fibers are coupled with small ordered area in the 28% modified sample. The 60% modified gel is more organized and reveals still small domains of unorganized fibers, but the 93% modified gels is totally organized in sheets.

This new organization of polysaccharide is surprising. These pictures validate the hypothesis of a new folding structure but moreover confirm the beta sheet organization of the polymer chains. The circular dichroism has shown that the modification of the primary alcohol of the D-galactose of the agarose repetition unit lead to the same change of folding of the secondary structure. The structure of the k-carrageenan hydrogels has been imaged by following the same protocol as for the agarose. The ESEM picture reveals that the modification of the k-carrageenan primary alcohol leads to the same highly organized structures forming thin sheets of the same kind as for 93% modified agarose gels. The same change of organization is shown for two different polysaccharide of the same family, which encourages the possibility of a general method for modifying polysaccharide organization and predict their secondary structure based on the protein models already existing, see FIG. 8 A4, A5, D4 and D5.

Figure 8:
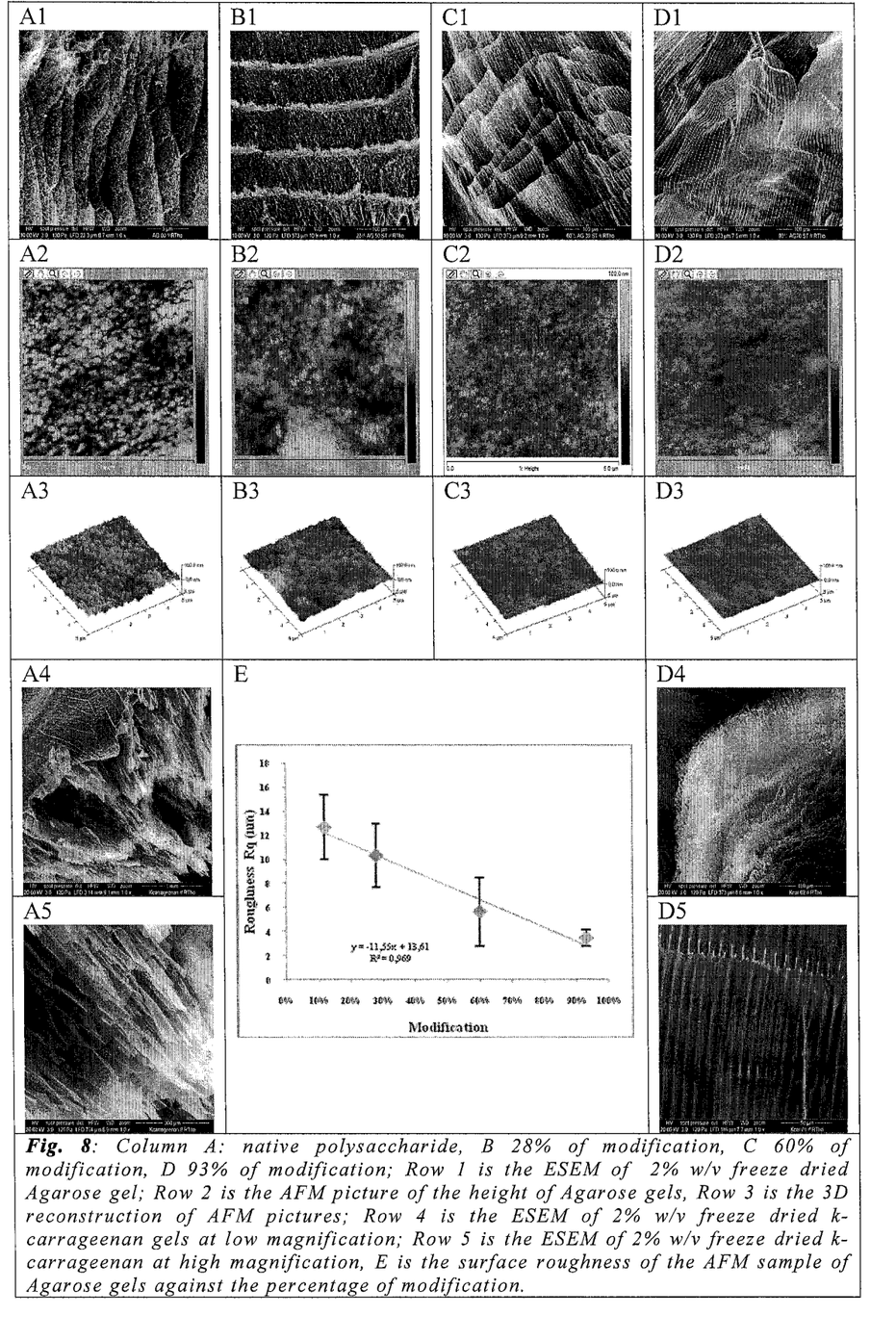
FIG. 8. Column A: native polysaccharide B 28% of modification, C 60% of modification, D 93% of modification; Row 1 is the ESEM of 2% w/v freeze dried agarose gel; Row 2 is the AFM picture of the height of agarose gels, Row 3 is the 3D reconstruction of AFM pictures; Row 4 is the ESEM of 2% w/v freeze dried k-carrageenan gels at low magnification; Row 5 is the ESEM of 2% w/v freeze dried k-carrageenan at high magnification, E is a diagram showing the surface roughness of the AFM sample of agarose gels plotted against the percentage of modification.

Cells which are cultivated on two-dimensional substrate show a dependence on the roughness of the substrate. Therefore the surface of the gel has been characterized in a semi-dry state by using an AFM. It can reveal the roughness of the surface. The height pictures highlight a loss of the relief, as the modification is increased, see FIG. 8 from A2 to D2. The tri-dimensional reconstruction allows visualizing clearly the loss of the roughness, see FIG. 8 from A2 to D2. The mathematic calculation of the roughness of the gel surface appears to be linearly related to the amount of carboxylic acid on the polymer backbone, see FIG. 8 E. The loss of the roughness can be explained by the smaller crosslinked points, aggregates calculated with the light scattering experiment, that are formed in the modified gels. The surface is smoother and the organization in sheets shown by the ESEM correlate the explanation of a smoother gel that has fibers more organized in a unilateral direction.

Example 1 a) Modification of Agarose

Agarose type I has been obtained from Calbiochem. TEMPO (((2,2,6,6-Tetramethylpiperidin-1-yl)oxyl), NaOCl, NaBH4, NaBr, EDC (1-ethyl-3-(3-dimethylaminopropyl) carbodiimide)), MES buffer (2-(N-morpholino)ethanesulfonic acid) have been obtained from Sigma Aldrich and used as received. Solution of 0.5 M NaOH have been freshly made every three-month as well as solution of 5 M HCl. Peptide GGGGRGDSP (SEQ ID NO: 3) has been obtained from Peptide International. Ethanol technical grade was used without any further purification. Deionized water was used for non sterile synthesis.

Agarose was modified under sterile conditions: all the chemicals were dissolved in autoclaved water and filtered with a 0.2 µm filter. All the glassware was autoclaved and the reaction was conducted under a laminar flow. Agarose (1 g) was autoclaved in MilliQ water. Autoclaved agarose was poured into a 3 necked round bottom flask. A mechanical stirrer was adapted to one of the neck. A pH-meter was adapted on the round bottom flask. The reactor was then cooled down to 0-5° C. and vigorously stirred. TEMPO (0.160 mmol, 20.6 mg) was added, NaBr (0.9 mmol, 0.1 g) and NaOCl (2.5 ml, 15% solution) was as well poured inside the reactor. The solution was adjusted to pH=10.8 with HCl and NaOH. The pH was maintained at 10.8 by adding NaOH. At the end of the reaction $NaBH_4$ (0.1 g) was added and pH=8 was reached. The solution was stirred for 1 hour and NaCl (0.2 mol, 12 g) and ethanol (500 ml) was added. The agarose was precipitated and extracted in a funnel. The two layers were then filtered on a frit glass. The agarose was then dialyzed in Spectra Pore 4, MWCO=12-14000 for 2 days and the water was changed two times. Prior dialysis in the membrane were left overnight in a 70% ethanol solution, 2 hours before use they were rinsed in autoclaved water. Finally the product was put on a Christ LD 2-8 LD plus at 0.1 mbar for the main drying and at 0.001 mbar during the desorption phase. Samples were put in round bottle flask and frozen in liquid nitrogen bath on a Rotary evaporator modified for this purpose. Thin layer of frozen solution were obtain on the flask wall reducing the lyophilization time.

b) Analytical Methods were Performed as Follows:

aa) Infrared Spectroscopy

FTIR spectra have been recorded on a Brucker vector 22. Sample were prepared with 2 mg of substance in 200 mg of KBr, then grinded and pressed under a 10 tons press for 10 min.

Bb) Nuclear Magnetic Resonance

Magic Angle Spinning NMR spectra were recorded in the solid state using a Brucker Avance DRX 500 spectrometer, freeze dried samples were put in a ceramic holder and spin at 7500 U/s.

cc) Rheology:

Rheology experiments were performed with an Anton Paar Physics MCR 301 equipped with a Peltier temperature cell. Sample were prepare as 2% w/v in deionized water, heated at 90° C. and stirred for 10 min until a clear solution was obtain. The liquid was then poured on the rheometer plate, pre-heated at 80° C., using a pipette. The solution was able to stabilize for 10 min before starting to record. A plate tool from Anton Paar: PPR25 was used for all the experiment. Sol-gel transition and frequency sweep were made using the same sample in a single cycle: 10 min equilibrium at 80° C., cooling down to 5° C. in 30 min and record of G' and G" every 1.5° C. at 1 rad/s with a deformation of 10%, stabilized at 5° C. for 30 min, heated up at 37° C. and stabilized for 30 min then the frequency sweep was recorded at 37° C. by increasing the rotation frequency from 0.01 rad/s up to 10 rad/s over 30 min with a deformation of 10%. Sol-gel transition temperature was calculated as the temperature where $\tan \theta = 0$.

Circular Dichroism:

Circular dichroism spectra were obtained using a Jasco spectropolarimeter J-810 equipped with a Peltier temperature cell Jasco PFD-425S. Solution of 0.15% w/v of agarose was made in Milli-Q water at 90° C. for 15 min then solution have been cooled down at 5° C. in the CD chamber for 30 min prior measurement. Each spectrum has been recorded three times and summed together. Each spectrum for a given modification is a mean of three different syntheses.

ee) Dynamic Light Scattering:

DLS has been done on a Beckman Coulter Delsa Nano C particle analyzer with a polystyrene cuvette of 1 cm. Agarose has been dissolved in Milli-Q water at 90° C. for 15 min to obtain a 0.15% w/v solutions that have been cooled down at room temperature for a day. The light scattering has been done at 15° C. and samples have been equilibrated for 30 min prior to measurement. For each measurement three measures have been done and an average has been calculated. Each point is a mean of three different syntheses.

ff) Zeta Potential:

Zeta potential has been measured on a Beckman Coulter Delsa Nano C particle analyzer. The same solutions have been used as for the light scattering experiment. Measurements have been made in a flow cell that has been aligned with the laser prior every measurement. Each measurement has been made three times and an average has been calculated, each spectrum for a given modification is a mean of three different syntheses.

gg) ESEM:

SEM pictures were obtain with a ref agarose gels of 2% w/v were prepared and 2 ml of this solution was frozen dried for 24 hours under 0.1 mbar vacuum in a 5 ml glass vial. The sample has then been vertically cut and the inside of the sample has been imaged at different magnification. Images shown here are representative of different areas of a given sample at different magnification, which have been reproduced with three different gels prepared from different batches.

hh) AFM:

AFM pictures were obtained with a Veeco Dimension 2100. Samples were prepared on a 3 mm microscopic glass holder that has been passivated. The glass slide was washed with 0.1 M NaOH and dry in the oven. The dry slides are then passivated with few drops of dichloromethylsilane. Two slides are sandwiched together to have a uniform passivation. After 10 min the slides are washed with water and the excess of dichloromethylsilane is washed with soap and the slides are dried. Slides side was prepared in a hydrophobic way. Agarose samples are prepared as 2% w/v gels and 25 µl of the solution is poured on an unmodified glass slide, a dichloromethylsilane passivated slide is then adjusted on top of the solution. Slides of 0.5 mm are put as spacer between the hydrophobic and the normal glass slide, the whole montage is then allowed to gel for 30 min at 4° C. The upper slide (hydrophobic) is after that removed and a thin layer of agarose gel is obtained, this gel is then allowed to stabilized at room temperature for 30 min before measurement in order to avoid any shrinkage or dilatation of the gel during the measurement.

ii) Molecular Dynamic:

MD simulations have been done using the Desmond package of the Maestro version 8.5 from Schrödinger. Initial conformation has been obtained from the x-ray structure of the agarose that has been downloaded from the PDB library. Modified agarose has been drawn from the PDB file directly inside the Maestro software. Implicit water model has been build using the Desmond tool, resulting in a 10 A square box build by following the TIP3 solution model. The simulations have been run in the model NPV at 300° K at atmospheric pressure for 15 ns. Analysis of the results was done using the VMD software and the tools available in the standard package.

Example 2

Peptide Modification of the Agarose

Functionalization of agarose with the $G_4RGDSP$ peptide (SEQ ID NO: 3) has been done by EDC peptide coupling. Agarose (30 mg, 0.25 µmol) was dissolved in autoclaved water; all the chemical and buffer were sterilized on a 0.2 µm filter, MES buffer was added and the solution reached a pH=4. The peptide was added (500 µg) and then EDC was added (200 mg) and the solution was stirred for two hours minutes at 40° C. to avoid any gel formation, The solution was then dialyzed in Spectra Pore 4 MWCO=12-14 kDa, water was changed three times and the sample was freeze dried. Prior dialysis; the membranes were left overnight in a 70% ethanol solution, 2 hours before use they were rinsed in autoclaved water.

Elementary Analysis

Samples have been analyzed on an Elementar Vario EL

Example 3: Use of Modified Extracellular Matrix for Biological Tests

Cell Culture:

Modified gels were prepared at a 2% w/v concentration in DMEM media and heated at 60° C. for 30 minutes in order to avoid any degradation of the RGD peptide. The temperature was adjusted to 37° C. and the culture media was completed with usual nutrients and cytokines. Human chondrocytes were obtain from ATCC and used between passage 3 and 5. Solution of agarose was mixed with the cells and then seeded in a 48 wells plate. The plate was then store at 4° C. for up to 30 min in order to allow the sol-gel transition to occur. The plates were then cultivated in a incubator at 37° C., 4% $CO_2$ for two weeks.

Cell Shape Factor:

All pictures have been taken on an Axio Observer A1, from Carl Zeiss, equipped with a DIC filter. Pictures were taken after 1, 5 and 14 days at different magnification in different area of the sample. The cell perimeter and cell area were then measured and the CSF was calculated. The results are a mean of three different batch of peptide modified Agarose which has been reproduce two times, which represent a total of 6 wells. Per well more than 100 cells were measured in order to have a meaning full CSF.

Real Time PCR:

At 7 days, 14 days and 21 days of cell culture in the gel, the media was removed and the gels were frozen at −80° C. overnight. The solids obtained were then crushed and digested with a CT AB buffer. Then extract using the Qiagen kits.

The invention claimed is:

1. A material comprising:
a modified agarose with at least partial β-sheet structure,
wherein said modified agarose is obtained from an agarose consisting of repeating disaccharide units exhibiting an alpha-helix structure by oxidation of at least one primary alcohol group in at least 11% of the disaccharide units of the agarose, and
wherein the modified agarose has a shear modulus G' in the range of from 10 Pa to $10^7$ Pa.

2. The material of claim 1 additionally comprising an unmodified polysaccharide.

3. The material of claim 2 wherein the unmodified polysaccharide is selected from the group consisting of agarose, a member of the carrageenan family, hyaluronic acid, heparin sulfate, dermatan sulfate, chondroitin sulfate, alginate, chitosan and pullulan.

4. The material of claim 3 wherein the unmodified polysaccharide is agarose.

5. The material of claim 1 additionally comprising living cells selected from the group consisting of chondrocytes, osteoblasts, osteoclasts, skin epithelial cells, intestinal epithelial cells, corneal epithelial cells, astrocytes, neurons, oligodendrocytes, smooth muscle cells, endothelial cells, cardiomyocytes, pancreatic islet cells, kidney epithelial cells, and umbilical cord cells.

6. The material of claim 1 additionally comprising living stem cells selected from the group consisting of embryonic stem cells, somatic stem cells, reprogrammed pluripotent somatic cells, induced pluripotent cells and amniotic stem cells.

7. The material of claim 1 wherein 50-95% of the disaccharide units are oxidized into a carboxylic acid group.

8. The material of claim 1, wherein the material is optically clear.

9. The material of claim 1 wherein 20-90% of the disaccharide units are oxidized into a carboxylic acid group.

10. The material of claim 1, wherein the material is sterile.

11. The material of claim 1, wherein the material is a regenerative implant.

12. The material in accordance with claim 11 wherein the regenerative implant is an artificial skin, an artificial blood vessel, a replacement of nerve tissue, a mucosal tissue or an artificial eye lens.

13. The material of claim 11 wherein the regenerative implant is in the form of a sheet, tube, or disc.

* * * * *

```
                        SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Lys Val Ala Val
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Gly Ser Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Arg Gly Asp Ser Pro
1               5
```